(12) United States Patent
Knoll et al.

(10) Patent No.: US 6,348,166 B1
(45) Date of Patent: Feb. 19, 2002

(54) METHOD FOR PRODUCING DI-ORGANO ALKALINE-EARTH COMPOUNDS

(75) Inventors: Konrad Knoll, Ludwigshafen (DE); Hans-Herbert Brintzinger, Taegerswilen (CH); Armin Weeber, Constance (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/555,593

(22) PCT Filed: Nov. 26, 1998

(86) PCT No.: PCT/EP98/07637

§ 371 Date: May 31, 2000

§ 102(e) Date: May 31, 2000

(87) PCT Pub. No.: WO99/29698

PCT Pub. Date: Jun. 17, 1999

(30) Foreign Application Priority Data

Dec. 9, 1997 (DE) .......................... 197 54 504

(51) Int. Cl.$^7$ .................................................. C07F 3/00
(52) U.S. Cl. .................................................. 260/665 R
(58) Field of Search ..................................... 260/665 R

(56) References Cited

U.S. PATENT DOCUMENTS

| 3,718,703 A | 2/1973 | West et al. | ............. 260/665 R |
| 3,763,251 A | 10/1973 | West et al. | ............. 260/665 R |
| 3,965,080 A | 6/1976 | Hargis et al. | ................ 526/183 |
| 4,012,336 A | 3/1977 | Hargis et al. | ........... 252/431 R |

OTHER PUBLICATIONS

Russ.Chem.Rev.,50 (6), 1981, 601–614.
JP Chem.Abst. vol. 118, No.25, Abst.254984.
JP Chem.Abst. vol. 91, No.6, Abst. 39948.
JP Chem. Abst. vol. 85, No. 10, Abst. 63411.

*Primary Examiner*—Porfirio Nazario-Gonzalez
(74) *Attorney, Agent, or Firm*—Keil & Weinkauf

(57) ABSTRACT

A process for the preparation of bisorganoalkaline earth metal compounds comprises reacting an organometallic compound $R_nM^2$ with an alkaline earth metal salt $M^1X_m$.

7 Claims, No Drawings

METHOD FOR PRODUCING DI-ORGANO ALKALINE-EARTH COMPOUNDS

The invention relates to a process for the preparation of bisorganoalkaline earth metal compounds.

The invention further relates to a process for the polymerization of anionically polymerizable monomers using a bisorganoalkaline earth metal compound prepared by the aforementioned process as polymerization initiator.

The synthesis of bisorganoalkaline earth metal compounds by reacting bisorganomercury compounds with elemental calcium, strontium or barium has been described in U.S. Pat. No. 3,718,703. Although this synthesis route produces the bisorganoalkaline earth metal compounds in good yields, it is not desirable in view of the use of poisonous mercury compounds.

The metallation of CH-acidic organic compounds with calcium, strontium or barium in aprotic, polar solvents has been described in U.S. Pat. Nos. 3,965,080 and 4,012,336. In this way, it is possible, for example, to prepare dixanthenylbarium.

Russian Chemical Reviews, Vol. 50, 1981, p. 601–614, gives a review of other possible syntheses and the use of organoalkaline earth metal compounds in the anionic polymerization of unsaturated monomers. Some of the known syntheses for organoalkaline earth metal compounds are complex or produce the desired compounds in low yields or contaminated with by-products.

Burkey et al. in Organometallics 12 (1993), pages 1331–1337 describe solvent-free alkaline earth metal metallocenes solvated with tetrahydrofuran (THF) which are obtained by reacting potassium cyclopentadienide with an alkaline earth metal iodide.

It is an object of the present invention to provide an economical process for the preparation of bisorganoalkaline earth metal compounds in high yields and high purity using readily available and easy-to-handle starting compounds.

We have found that this object is achieved by a process for the preparation of bisorganoalkaline earth metal compounds which comprises reacting an organometallic compound $R_nM^2$ having a covalent metal-carbon bond content with an alkaline earth metal salt $M^1X_m$.

We have also found a process for the polymerization of anionically polymerizable monomers using, as polymerization initiator, a bisorganoalkaline earth metal compound prepared by a process as claimed in any of claims 1 to 5.

The organometallic compounds which may be used for the novel process for the preparation of bisorganoalkaline earth metal compounds are any customary organometallic compounds having a covalent metal-carbon bond content. Preference is given to organolithium, organosodium, organopotassium or organomagnesium compounds, in particular organolithium or organomagnesium compounds, which are usually more soluble. Suitable organic groups R are preferably σ-bonded hydrocarbons having from 1 to 25 carbon atoms, in particular $C_1$–$C_{25}$-alkyl, such as methyl, ethyl, n-propyl, isopropyl, n-butyl, isobutyl, tert-butyl, pentyl, hexyl, heptyl, octyl, nonyl, dodecyl, octadecyl, $C_6$–$C_{25}$-aryl, such as phenyl or substituted phenyl, such as 3,5-dimethylphenyl, p-t-butylphenyl, p-octylphenyl, p-dodecylphenyl, o-, m-, p-tolyl, biphenyl, naphthyl, aralkyl, such as benzyl, phenylethyl, 2-phenylpropyl, 6-phenylhexyl, p-methylphenylethyl, p-t-amylbenzyl, $C_3$–$C_{12}$-alkenyl, such as vinyl, allyl, 3-butenyl., 4-hexenyl, $C_3$–$C_{12}$-cycloalkyl, such as cyclopropyl, cyclobutyl, cyclopentyl, cyclohexyl, cyclooctyl, $C_3$–$C_{12}$-cycloalkenyl, such as cyclohexenyl or cyclooctenyl. The organic groups R may carry functional groups which are inert to the metal-carbon bond. Examples thereof are trimethylsilyl, trimethylsiloxy, ether, dialkylamino or cycloalkylamino groups. The integer n is 1 where $M^2$ is an alkali metal, or 2 when $M^2$ is magnesium. Particularly preferred organometallic compounds are benzyllithium and dibenzylmagnesium. The organometallic compounds are often in the form of adducts with solvents such as tetrahydrofuran, dioxane or complexing agents such as tetramethylethylenediamine or crown ethers. The preparation of the organometallic compounds is known per se. They can, for example, be prepared by reacting lithium or magnesium with the appropriate organohalides in organic solvents such as pentane, hexane or diethyl ether. Suitable alkaline earth metals $M^1$ in the alkaline earth metal salts $M^1X_m$ are preferably calcium, strontium and barium. They are used in the form of their salts X as halides, amides, phosphides, alkyl oxides or aryl oxides, m being an integer 1 or 2 depending on the valency of X. Preference is given to the readily available bis (trimethylsilyl)amides or 2,4,6-tris(tert-butyl)phenoxides. The alkaline earth metal salts can be obtained, for example, by reacting the alkaline earth metals with the corresponding hydrohalic acids, amines, phosphines, alkyl hydroxides or aryl hydroxides with the elimination of hydrogen. Processes for the preparation of ether complexes by reacting calcium, strontium and barium in ethereal solution saturated with ammonia gas are described, for example, by S. R. Drake et al., Main Group Chemistry 14) 1991, page 243, Polyhedron (12) 1993, page 2307–2311 or Journal of the Chemical Society, Chemical Communications 1991, page 517–519.

The process is preferably used for the preparation of organoalkaline earth metal compounds $R_2M^1$ having two identical organic groups R, i.e. homoleptic alkaline earth metal compounds.

When using mixed organometallic compounds, for example butyloctylmagnesium, or mixtures of different organometallic compounds, heteroleptic bisorganoalkaline earth metal compounds are also available.

The novel reaction of the organometallic compounds $R_nM^2$ with the alkaline earth metal salts $M^1X_m$ is preferably carried out in an organic solvent or solvent mixture in which the bisorganoalkaline earth metal compounds produced have the lowest solubility product of all starting materials and products. Suitable solvents or solvent components are aliphatic or aromatic, aprotic solvents, such as aliphatic or cycloaliphatic ethers, for example dimethyl ether, diethyl ether, dibutyl ether, diisopropyl ether, dioxane or tetrahydrofuran, aliphatic and cycloaliphatic hydrocarbons, such as pentane, hexane, octane, cyclohexane or cyclooctane, or aromatic hydrocarbons, such as toluene or ethylbenzene.

The organometallic compound $R_nM^2$ is generally reacted with the alkaline earth metal salt $M^1X_m$ in stoichiometrically equivalent amounts.

In a preferred embodiment, the alkaline earth metal salt is dissolved in a polar, aprotic solvent, to which a solution of the organometallic compound is added dropwise, and the precipitate which forms is filtered off and washed.

The resulting bisorganoalkaline earth metal compound can be further purified where appropriate by the known methods of organometallic chemistry. For example, the bisorganoalkaline earth metal compound may be dissolved in a solvent and admixed or covered with a layer of a precipitant.

The temperature for the reaction is unimportant. It does of course depend on the melting points and boiling points of the solvents used, and also on the stability of the bisorganoalkaline earth metal compound. The reaction is usually carried out in the range from −80 to +50° C., preferably in the range from 0 to 30° C.

The bisorganoalkaline earth metal compounds prepared by the novel process are suitable as polymerization initiators for anionically polymerizable monomers such as dienes, styrene, acrylates, methacrylates, acrylonitriles and vinyl chloride. They are particularly suitable for the homo- and copolymerization of butadiene, isoprene and styrene.

To improve the thermal stability (the bisorganoalkaline earth metal compounds of lower alkyls are usually thermally unstable at room temperature) but also to improve the solubility, the bisorganoalkaline earth metal compounds may be reacted with 1,1-diphenylethylene. This is of particular importance if the polymerization is to be carried out in the absence of polar solvents.

EXAMPLES

All operations were carried out under protective gas and in solvents freshly distilled over sodium.

Barium bis(bistrimethylsilyl)amide*2 tetrahydrofuran was obtained by the procedure in B. A. Vaartstra et al., Inorganic Chemistry 1991 (Vol. 30), page 121–125, by reacting barium with Strontium bis(bistrimethylsilyl)amide*2 tetrahydrofuran was obtained by the procedure in S. R. Drake et al., Journal of the Chemical Society, Chemical Communications 1991, page 517–519.

Strontium bis(2,4,6-tri-tert-butylphenoxide)*3 tetrahydrofuran was obtained by the procedure of S. R. Drake et al., Polyhedron (11) 1992, page 1995–2007.

Dibenzylmagnesium*dioxane was obtained by the Grignard reaction of magnesium with benzyl bromide according to Y. Pocker et al., Journal of the American Chemical Society, 1968 (Vol. 90) page 6764.

Benzyllithium*tetramethylethylenediamine was prepared by the procedure given in B. J. Wakefield, Organolithium Methods, Academic Press 1988, on page 38.

Preparation of dibenzylbarium

Example 1

Preparation of dibenzylbarium by reacting barium bis(bistrimethylsilyl)amide*2 tetrahydrofuran and dibenzylmagnesium*dioxane A solution of 8.6 g (14.4 mmol) of barium bis(bistrimethylsilyl)amide*2 THF in 50 ml of toluene/diethyl ether (4/1 vol.-%) was added dropwise at 25° C. to a solution of 4.35 g (14.8 mmol) of dibenzylmagnesium*dioxane in 75 ml of toluene/diethyl ether (4/1 vol.-%) over the course of 10 minutes, and the mixture was stirred for 14 hours. The yellow precipitate formed was then filtered off and washed with 2×20 ml of diethyl ether. The residue was taken up in 30 ml of tetrahydrofuran and covered with a layer of 60 ml of pentane. After 24 hours a first precipitate had formed. To complete crystallization the two phases were mixed, and the precipitate was filtered off and washed with 2×20 ml of diethyl ether. The dibenzylbarium was obtained in a yield of 1.82 g (5.7 mmol), corresponding to 40%. $^1$H-NMR characterization produced the following results: 1.99 (s, 4H), 5.37 (t, 2H), 5.75 (d, 4H), 6.42 (t, 4H). (All data in ppm, d8-THF solvent, down field signals of the incompletely deuterated solvent at 3.58 ppm).

Example 2

Preparation of dibenzylbarium by reacting barium bis(bistrimethylsilyl)amide*2 tetrahydrofuran and benzyllithium*tetramethylethylenediamine A solution of 10.67 g (49.8 mmol) of benzyllithium*tetramethylethylenediamine in 150 ml of diethyl ether was added dropwise at 25° C. to a solution of 15 g (24.9 mmol) of barium bis(bistrimethylsilyl)amide*2 THF in 100 ml of diethyl ether over the course of 20 minutes, and the mixture was stirred for 14 hours. The orange precipitate formed was then filtered off and washed with 3×20 ml of diethyl ether. The dibenzylbarium was obtained in a yield of 7.44 g (23.3 mmol), corresponding to 93%. $^1$H-NMR characterization produced the following results: 1.99 (s, 4H), 5.37 (t, 2H), 5.75 (d, 4H), 6.42 (t, 4H). (All data in ppm, d8-THF solvent, down field signals of the incompletely deuterated solvent at 3.58 ppm).

Example 3

Preparation of dibenzylstrontium by reacting strontium bis(bistrimethylsilyl)amide*2 tetrahydrofuran and benzyllithium*tetramethylethylenediamine.

A solution of 0.38 g (1.77 mmol) of benzyllithium*tetramethylethylenediamine in 20 ml of diethyl ether was added dropwise at 25° C. to a solution of 0.50 g (0.90 mmol) of strontium bis(bistrimethylsilyl)amide*2 THF in 10 ml of diethyl ether over the course of 5 minutes. An orange precipitate quickly formed, which, after stirring for a further 14 hours, was filtered off and washed with diethyl ether.

Example 4

Preparation of dibenzylstrontium by reacting strontium bis(2,4,6-tri-tert-butylphenoxide)*3 tetrahydrofuran and benzyllithium*tetramethylethylenediamine.

A solution of 1.39 g (6.5 mmol) of benzyllithium*tetramethylethylenediamine in 25 ml of toluene was added dropwise at 25° C. to a solution of 2.51 g (3.02 mmol) of strontium bis(2,4,6-tri-tert-butylphenoxide)*3 tetrahydrofuran in 15 ml of toluene over the course of 10 minutes. An orange precipitate quickly formed, which, after stirring for a further 14 hours, was filtered off and washed with 20 ml of toluene.

Example 5

Preparation of bis(1,1,3-triphenylpropyl)barium*2 tetrahydrofuran:

0.19 ml (1.07 mmol) of 1,1-diphenylethylene (DPE) was added at 25° C. to a solution of 150 mg (0.47 mmol) of dibenzylbarium (from Example 2) in 20 ml of tetrahydrofuran, as a result of which the red coloration of the solution quickly intensified. The mixture was stirred for a further 14 hours and the solvent was removed under a high vacuum. To purify the product further, it was dissolved in 30 ml of benzene and filtered off from insoluble constituents. The filtrate was evaporated to dryness under a high vacuum and the black-violet residue was washed with 40 ml of pentane. $^1$H-NMR characterization produced the following results: 1.27 (m, 8H, THF), 2.67 (m, 4H, CH2), 2.77 (m, 4H, CH2), 3.29 (m, 8H, THF), 6.12 (t, 4H, para), 6.75 (t, 8H, meta), 6.85 (d, 8H, ortho), 7.10 (m, 5H, 3-phenyl). (All data in ppm, $C_6D_6$ solvent, incompletely deuterated solvent at 7.15 ppm).

Example 6

0.21 ml (1.14 mmol) of 1,1-diphenylethylene (DPE) was added at 25° C. to a suspension of 170 mg (0.53 mmol) of dibenzylbarium in 20 ml of toluene and 1 ml of tetrahydrofuran. The mixture was stirred for a further 14 hours and a deep red solution was formed from the suspension.

Example 7

Example 6 was repeated except that ethylbenzene was used instead of toluene.

Example 8

Polymerization of styrene:

A solution of 48 g (0.46 mol) of styrene in 450 g of cyclohexane was titrated with an initiator solution as in Example 5 (0.03 mol/l of bis(1,1,3-triphenylpropyl)

barium*2 tetrahydrofuran in ethylbenzene) until there was a slight red coloration. 7.5 ml of the initiator solution were added to the mixture which was then polymerized for half an hour at from 58 to 65° C. Polymerization was then terminated using 10 ml of isopropanol. The polystyrene obtained had a number-average molecular weight Mn of 99,000 g/mol, a weight-average molecular weight of 145,000 g/mol and a dispersity D of 1.46 (gel permeation chromatography in tetrahydrofuran relative to a polystyrene standard).

We claim:

1. A process for the preparation of bisorganoalkaline earth metal compounds, which comprises reacting an organometallic compound having a covalent metal-carbon bond content with an alkaline earth metal salt.

2. A process for the preparation of bisorganoalkaline earth metal compounds as claimed in claim 1, which comprises reacting an organometallic compound $R_nM^2$ with an alkaline earth metal salt $M^1X_m$, where $M^1$ is Ca, Sr or Ba, $M^2$ is Li, Na, K or Mg, R is a metal-carbon-σ-bonded hydrocarbon having from 1 to 25 carbon atoms, X is halide, amide, phosphide, alkyl oxide or aryl oxide and n and m are integers 1 or 2, depending on the valency of $M^1$ or $M^2$ and X.

3. A process as claimed in claim 2, wherein the organic group R is $C_1$–$C_{25}$-alkyl, $C_6$–$C_{25}$-aryl, $C_3$–$C_{12}$-alkenyl, $C_3$–$C_{12}$-cycloalkyl or $C_3$–$C_{12}$-cycloalkenyl.

4. A process as claimed in claim 2, wherein the bisorganoalkaline earth metal compound is a homoleptic organoalkaline earth metal compound $R_2M^1$ having two identical organic groups R.

5. A process as claimed in claim 1, which comprises reacting barium bis(bistrimethylsilyl)amide or strontium bis(bistrimethylsilyl)amide or barium bis(2,4,6-tri-tert-butylphenoxide) or strontium bis(2,4,6-tri-tert-butylphenoxide) with benzyllithium or dibenzylmagnesium.

6. A process as claimed in claim 1, which comprises carrying out the reaction in an organic solvent or solvent mixture in which the bisorganoalkaline earth metal compound formed has the lowest solubility product of all starting materials and products.

7. A process as claimed in claim 1, which comprises carrying out the reaction in diethyl ether, toluene or a mixture thereof.

* * * * *